(12) United States Patent
Joshi et al.

(10) Patent No.: US 8,815,835 B2
(45) Date of Patent: Aug. 26, 2014

(54) 9-AMINONOSCAPINE AND ITS USE IN TREATING CANCERS, INCLUDING DRUG-RESISTANT CANCERS

(71) Applicant: Emory University, Atlanta, GA (US)

(72) Inventors: Harish C. Joshi, Decatur, GA (US); Ritu Aneja, Lilburn, GA (US); Surya N. Vangapandu, Alpharetta, GA (US)

(73) Assignee: Emory University, Atlanta, GA (US)

( * ) Notice: Subject to any disclaimer, the term of this patent is extended or adjusted under 35 U.S.C. 154(b) by 35 days.

(21) Appl. No.: 13/762,753

(22) Filed: Feb. 8, 2013

(65) Prior Publication Data

US 2013/0150332 A1    Jun. 13, 2013

Related U.S. Application Data

(62) Division of application No. 13/062,481, filed as application No. PCT/US2009/056062 on Sep. 4, 2009, now Pat. No. 8,394,957.

(60) Provisional application No. 61/094,679, filed on Sep. 5, 2008.

(51) Int. Cl.
*A01N 33/26* (2006.01)
*A01N 43/42* (2006.01)

(52) U.S. Cl.
USPC ............................. 514/150; 514/290

(58) Field of Classification Search
CPC ................................. A61K 31/4355
USPC .................................. 514/150, 291
See application file for complete search history.

(56) References Cited

U.S. PATENT DOCUMENTS

| | | | |
|---|---|---|---|
| 4,970,212 | A | 11/1990 | Nowicky |
| 6,376,516 | B1 | 4/2002 | Joshi et al. |
| 2010/0227878 | A1 | 9/2010 | Joshi et al. |
| 2011/0294844 | A1 | 12/2011 | Joshi et al. |

FOREIGN PATENT DOCUMENTS

| | | |
|---|---|---|
| WO | 9908528 A1 | 2/1999 |
| WO | 2007133112 A1 | 11/2007 |

*Primary Examiner* — Nizal Chandrakumar
(74) *Attorney, Agent, or Firm* — Hultquist, PLLC; David Bradin

(57) ABSTRACT

9-aminonoscapine, prodrugs thereof, and pharmaceutically acceptable salts thereof, are disclosed. Pharmaceutical compositions including 9-aminonoscapine, and methods of preparation and use thereof are disclosed. 9-aminonoscapine is a noscapine analog that can be used to treat and/or prevent a wide variety of cancers, including drug resistant cancers, by binding tubulin and inducing apoptosis selectively in tumor cells (ovarian and T-cell lymphoma) resistant to paclitaxel, vinblastine and teniposide. 9-aminonoscapine can perturb the progression of cell cycle by mitotic arrest, followed by apoptotic cell death associated with increased caspase-3 activation and appearance of TUNEL-positive cells. Thus, 9-aminonoscapine is a novel therapeutic agents for a variety of cancers, including ovarian and T-cell lymphoma cancers, even those that have become drug-resistant to currently available chemotherapeutic drugs.

4 Claims, 2 Drawing Sheets

9-AMINONOSCAPINE AND ITS USE IN TREATING CANCERS, INCLUDING DRUG-RESISTANT CANCERS

This application is a division of U.S. patent application Ser. No. 13/062,481 filed Mar. 4, 2011, which is a U.S. national phase application under the provisions of 35 U.S.C. §371 of International Patent Application No. PCT/US09/56062 filed Sep. 4, 2009, which in turn claims priority of U.S. Patent Application No. 61/094,679 filed Sep. 5, 2008. The disclosures of such international patent application and US priority patent applications are hereby incorporated herein by reference in their respective entireties, for all purposes.

This invention was made with government support under Grant 1 R01 CA095317-01A2 awarded by the National Institutes of Health. The government has certain rights in the invention.

FIELD OF THE INVENTION

The present invention relates to the noscapine analog 9-aminonoscapine, pharmaceutical compositions incorporating 9-aminonoscapine analog, and methods of using the compound and compositions to treat cancers, including drug resistant cancers.

BACKGROUND OF THE INVENTION

Microtubules are major cytoskeletal structures responsible for maintaining genetic stability during cell division (Sammak and Borisy, 1987; McIntosh, 1994; Desai and Mitchinson, 1997). The dynamics of these polymers is absolutely crucial for this function that can be described as their growth rate at the plus ends, catastrophic shortening, frequency of transition between the two phases, pause between the two phases, their release from the microtubule organizing center and treadmilling (Margolis and Wilson, 1981; Mitchison and Kirschner, 1984; Kirschner and Mitchison, 1986; Margolis and Wilson, 1998; Jordan and Wilson, 2004). Microtubule lattice also serves as tracks for the axonal transport of organelles driven by anteriograde and retrograde molecular motors to generate and maintain axonal integrity (Joshi, 1998; Nogales, 2000). Interference with microtubule dynamics often leads to programmed cell death and thus microtubule-binding drugs are currently used to treat various malignancies in the clinic (Jordan and Wilson, 2004). Although useful, currently used microtubule drugs such as vincas and taxanes are limited due to the emergence of drug resistance. There have been multiple mechanisms for antimicrotubule drug resistance including overexpression of drug-efflux pumps, misexpression of tubulin isotypes, and perhaps mutational lesions in tubulin itself (Ranganathan et al., 1996; Giannakakou et al., 1997; Monzo et al., 1999; Dumontet et al., 2005).

The pharmacological profile of microtubule-binding agents, however, has not been ideal. Most of them need to be infused over long periods of time in the clinic because they are not water-soluble, and can cause hypersensitive reactions due to the vehicle solution (Rowinsky, 1997). Furthermore, normally dividing cells within the healthy tissues such as intestinal crypts, hair follicles, and the bone marrow are also vulnerable to these agents, leading to toxicities (Rowinsky, 1997). In addition, nerve cells dependent on molecular traffic over long distances undergo degenerative changes causing peripheral neuropathies (Pace et al., 1996; Crown and O'Leary, 2000; Theiss and Meller, 2000; Topp et al., 2000).

Noscapine ((S)-6,7-dimethoxy-3-((R)-4-methoxy-6-methyl-5,6,7,8-tetrahydro[1,3]-dioxolo-[4,5-g]isoquinolin-5-yl)isobenzo-furan-1(3H)-one), a safe antitussive agent for over 40 years, binds tubulin, arrests dividing cells in mitosis and induces apoptosis (Ye et al., 1998). It is well-tolerated in humans and has been shown to be non-toxic in healthy volunteers, including pregnant mothers (Dahlstrom et al., 1982; Karlsson et al., 1990; Jensen et al., 1992).

Unlike the other microtubule-targeting drugs, noscapine does not significantly change the microtubule polymer mass even at high concentrations. Instead, it suppresses microtubule dynamics by increasing the time that microtubules spend in an attenuated (pause) state when neither microtubule growth nor shortening is detectable (Landen et al., 2002). Thus, noscapine-induced suppression of microtubule dynamics, even though subtle, is sufficient to interfere with the proper attachment of chromosomes to kinetochore microtubules and to suppress the tension across paired kinetochores (Zhou et al., 2002a). This represents an improvement over the taxanes, the microtubule-bundling agents or overpolymerizers, and vincas, the depolymerizers, that cause toxicities in mitotic and post mitotic neurons at elevated doses.

Noscapine thus effectively inhibits the progression of various cancer types both in cultured cells and in animal models with no obvious side effects (Ye et al., 1998; Landen et al., 2002; Zhou et al., 2002b; 2003; Landen et al., 2004). Surprisingly, the apoptosis is much more pronounced in cancer cells compared with normal healthy cells (Landen et al., 2002).

It would be desirable to have compounds, compositions and methods for preventing and/or treating various types of cancer, without significant associated side effects, that provide increased anti-cancer properties to that of noscapine. The present invention provides such a compound, compositions and methods.

SUMMARY OF THE INVENTION 9-aminonoscapine, pharmaceutically acceptable salts, prodrugs and metabolites thereof, (herein referred to as the "compounds"), pharmaceutical compositions including the compounds, and methods of preparation and use thereof are disclosed. 9-aminonoscapine is a noscapine analog, with an amine group at the 9-position of the isoquinoline ring. The synthesis, characterization and an evaluation of the anti-tumor potential of 9-amino-Nos is described herein.

9-aminonoscapine binds tubulin, and effectively inhibits cell proliferation of 1A9 (ovarian cancer cells) and its paclitaxel-resistant variant (1A9/PTX22), and human lymphoblastoid cells CEM, and its vinblastine-(CEM/VLB100) and teniposide-(CEM/VM-1-5) resistant variants.

Treatment with 9-aminonoscapine halts cell cycle progression in cells due to the checkpoints governed by many crucial genes that are mutated in cancer cells. Therefore, we hypothesize that normal cells resume normal cell cycle as the drug clears from the system (excretion, metabolism etc). However, due to checkpoint lesions in cancer cells, they do not arrest for longer times but undergo mitotic catastrophic and apoptosis. Therefore, 9-aminonoscapine only affects cancer cells and spares the normal cells.

The pharmaceutical compositions include an effective amount of the compounds described herein, along with a pharmaceutically acceptable carrier or excipient. When employed in effective amounts, the compounds can act as a therapeutic agent to prevent and/or treat a wide variety of cancers, particularly drug resistant cancers, and are believed to be both safe and effective in this role. Representative cancers that can be treated and/or prevented include drug-resistant ovarian cancer, drug resistant T-cell lymphoma, leukemia, non-small cell lung, colon, central nervous system (CNS), melanoma, renal, ovarian, breast and prostate cancer.

The foregoing and other aspects of the present invention are explained in detail in the detailed description and examples set forth below.

BRIEF DESCRIPTION OF THE DRAWINGS

In FIG. 1A, the tubulin fluorescence emission spectrum is quenched by Nos, and in FIG. 1B, the tubulin fluorescence emission spectrum is quenched by 9-aminonoscapine, in a concentration-dependent manner. FIG. 1C is a double reciprocal plot showing a dissociation constant ($K_d$) of 152±1 µM for Nos binding to tubulin, and FIG. 1D is a double reciprocal plot showing a dissociation constant ($K_d$) of 14±1 µM for 9-aminonoscapine binding to tubulin. Values are mean±SD for four experiments performed in triplicate (p<0.05). The graphs shown are a representative of four experiments performed.

DETAILED DESCRIPTION OF THE INVENTION

Figure 1:
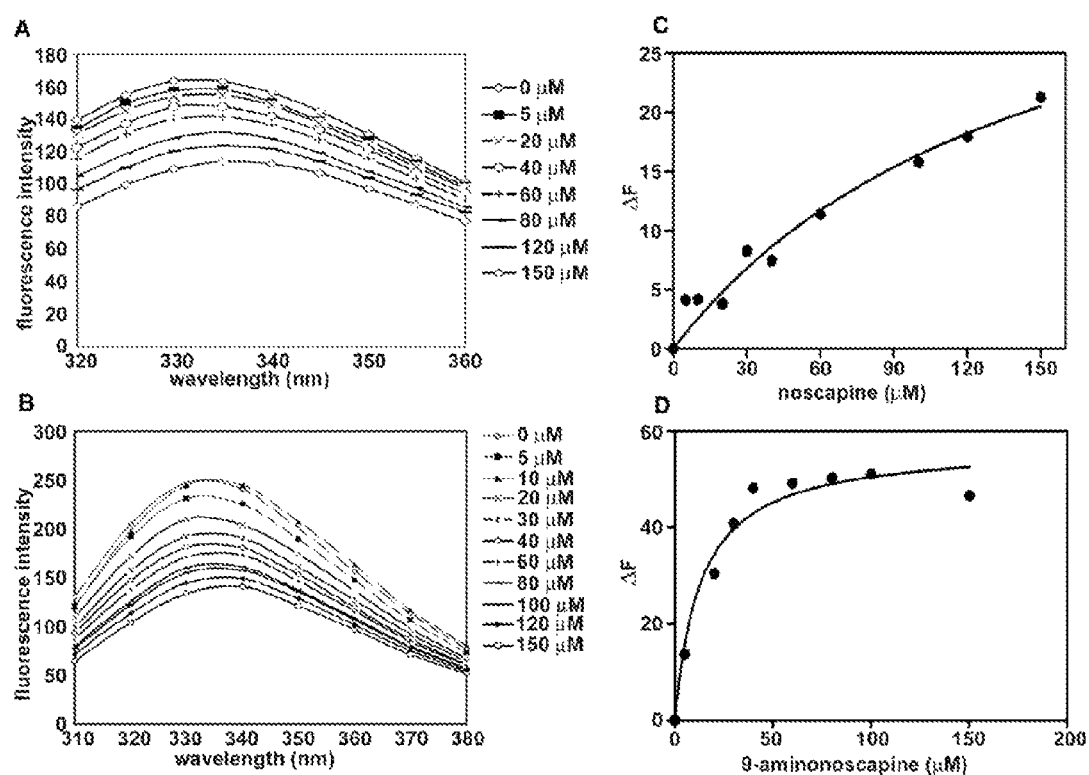
FIGS. 1A-D are charts showing the fluorescence quenching of tubulin by 9-aminonoscapine.
Figure 2:
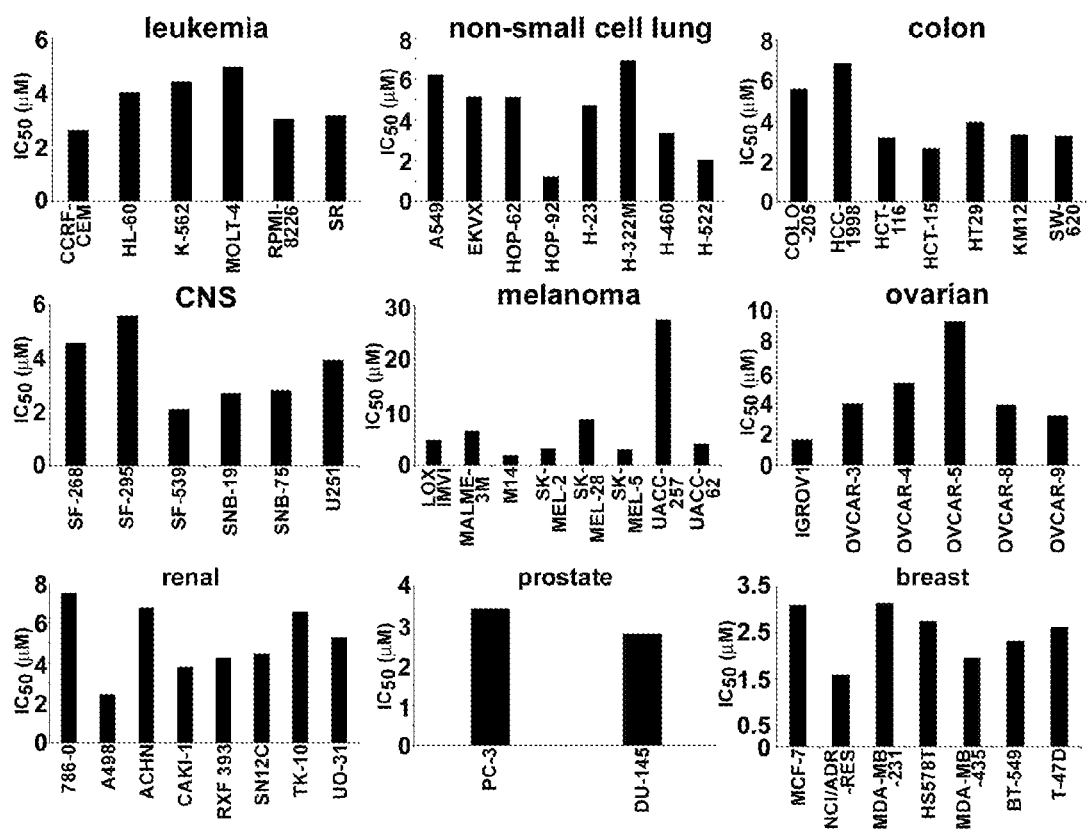
FIG. 2 is a bar graph showing the $IC_{50}$ values for the in vitro treatment of various cancer cell types with 9-aminonoscapine (µM)

Compounds, pharmaceutical compositions including the compounds, and methods of preparation and use thereof are disclosed.

The following definitions will be useful in understanding the metes and bounds of the invention as described herein.

I. 9-Aminonoscapine

The compounds described herein include 9-aminonoscapine ((S)-6,7-dimethoxy-3-((R)-4-methoxy-6-methyl-9-amino-5,6,7,8-tetrahydro-[1,3]dioxolo[4,5-g]isoquinolin-5-yl)isobenzofuran-1(3H)-one)), a noscapine analog with an amine group at the 9-position of the quinoline ring, prodrugs or metabolites of this compound, and pharmaceutically acceptable salts thereof. 9-amino-noscapine has the structure shown below.

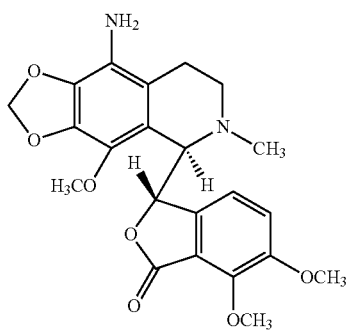 [SMILES: COc1ccc2c(c1OC)C(=O)O[C@@H]2[C@H]1c2c(c(N)c3c(c2OC)OCO3)CCN1C]

The compound can exist in varying degrees of enantiomeric excess.

The compound can be in a free base form or in a salt form (e.g., as pharmaceutically acceptable salts).

Pharmaceutically-Acceptable Salts

Examples of suitable pharmaceutically acceptable salts include inorganic acid addition salts such as sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with an acidic amino acid such as aspartate and glutamate; alkali metal salts such as sodium and potassium; alkaline earth metal salts such as magnesium and calcium; ammonium salt; organic basic salts such as trimethylamine, triethylamine, pyridine, picoline, dicyclohexylamine, and N,N'-dibenzylethylenediamine; and salts with a basic amino acid such as lysine and arginine. The salts can be in some cases hydrates or ethanol solvates. The stoichiometry of the salt will vary with the nature of the components.

Pharmaceutically acceptable salts may be obtained using standard procedures well known in the art, for example by reacting the amine group with a suitable acid affording a physiologically acceptable anion. In one embodiment, the salt is a hydrochloride salt of the compound.

Prodrugs and Derivatives

The active compound can be administered as any salt or prodrug that upon administration to the recipient is capable of providing directly or indirectly the parent compound, or that exhibits activity itself. Non-limiting examples include forms of 9-aminonoscapine in which the amine group has been alkylated, acylated, or otherwise modified (a type of "pharmaceutically acceptable prodrug").

Further, the modifications can affect the biological activity of the compound, in some cases increasing the activity over the parent compound. This can easily be assessed by preparing the salt or prodrug and testing its anticancer or other activity according to the methods described herein, or other methods known to those skilled in the art.

Prodrug forms of the compound include the following types of derivatives where each R group individually can be hydrogen, substituted or unsubstituted alkyl, aryl, alkenyl, alkynyl, heterocycle, alkylaryl, aralkyl, aralkenyl, aralkynl, cycloalkyl or cycloalkenyl groups.

(a) Carboxamides, —NHC(O)R
(b) Carbamates, —NHC(O)OR
(c) (Acyloxy)alkyl Carbamates, NHC(O)OROC(O)R
(d) Enamines, —NHCR(=CHCO$_2$R) or —NHCR(=CHCONR$_2$)
(e) Schiff Bases, —N=CR$_2$
(f) Mannich Bases (from carboximide compounds), RCONHCH$_2$NR$_2$ As used herein, alkyl refers to $C_{1-8}$ straight, branched, or cyclic alkyl groups, and alkenyl and alkynyl refers to $C_{2-8}$ straight, branched or cyclic moieties that include a double or triple bond, respectively. Aryl groups include $C_{6-10}$ aryl moieties, specifically including benzene. Heterocyclic groups include $C_{3-10}$ rings which include one or more O, N, or S atoms. Alkylaryl groups are alkyl groups with an aryl moiety, and the linkage to the nitrogen at the 9-position on the noscapine framework is through a position on the alkyl group. Arylalkyl groups are aryl groups with an alkyl moiety, and the linkage to the nitrogen at the 9-position on the noscapine framework is through a position on the aryl group. Aralkenyl and aralkynyl groups are similar to aralkyl groups, except that instead of an alkyl moiety, these include an alkenyl or alkynyl moiety. Substituents for each of these moieties include halo, nitro, amine, thio, hydroxy, ester, thioester, ether, aryl, alkyl, carboxy, amide, azo, sulfonyl, and Other prodrugs include prodrugs that are converted in biological milieu via ester hydrolysis via an enzymatic route rather than chemical hydrolysis, for example, by serine-dependent esterases. Representative prodrugs of this type are described, for example, in Amsberry et al., "Amine Prodrugs Which Utilize Hydroxy Amide Lactonization. II. A Potential Esterase-Sensitive Amide Prodrug," *Pharmaceutical Research*, Volume 8(4): 455-461(7) (April 1991).

Azo-based prodrugs can also be used. For example, bacterial reductases can use reductive cleavage to convert the following azo prodrug in vivo to the active form.

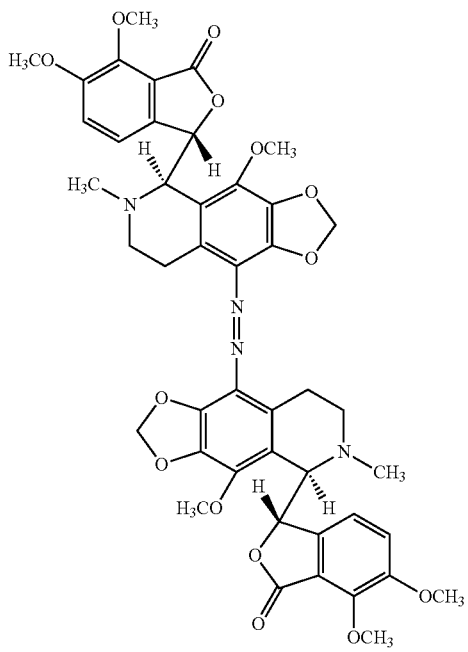 [SMILES: COc1ccc2c(c1OC)C(=O)O[C@@H]2[C@H]1c2c(c(N=Nc3c4c(c(OC)c5c3OCO5)[C@H]([C@H]3OC(=O)c5c3ccc(OC)c5OC)N(C)CC4)c3c(c2OC)OCO3)CCN1C]

II. Method of 9-Aminonoscapine Synthesis
Experimental
General:
$^1$H NMR and $^{13}$C NMR spectra were measured in CDCl$_3$ on INOVA 400 NMR spectrometer. All proton NMR spectra were recorded at 400 MHz and were referenced with residual chloroform (7.27 ppm). All carbon NMR spectra were recorded at 100 MHz and were referenced with 77.27 ppm resonance of residual chloroform. Abbreviations for signal coupling are as follows: s, singlet; d, doublet; t, triplet; q, quartet; m, multiplet. Infrared spectra were recorded on sodium chloride discs on Mattson Genesis II FT-IR. High resolution mass spectra were collected on Thermo Finnigan LTQ-FT Hybrid mass spectrophotometer using 3-nitrobenzyl alcohol, in some cases with addition of LiI as a matrix. Melting points were determined using a Thomas Hoover melting point apparatus and were uncorrected. All reactions were conducted in oven-dried (125° C.) glassware under an atmosphere of dry argon. All common reagents and solvents were obtained from commercial suppliers and used without further purification unless otherwise indicated. Solvents were dried by standard methods. The reactions were monitored by thin layer chromatography (TLC) using silica gel 60 F254 (Merck) precoated aluminum sheets. Flash chromatography was carried out on standard grade silica gel (230-400 mesh).

Synthesis of 9-aminonoscapine was shown in Scheme 1. Briefly, noscapine (1) was dissolved minimum amount of 48% hydrobromic acid and then cautiously added freshly prepared bromine water. The reaction mixture stirred for 1 h at 25° C. and the resultant mixture was basified to pH 10 to afford 9-bromonoscapine in 82% yield. Refluxing compound 2 in DMF with sodium azide and sodium iodide for 15 hours gave its azido derivative (3) in quantitative yield. Reduction of azido derivative with tin chloride in the presence of thiophenol and triethylamine in THF for 2 h at 25° C. afforded the title compound, 9-aminonoscapine (4) in 83% yield.

Scheme 1. Synthesis of 9-aminonoscapine

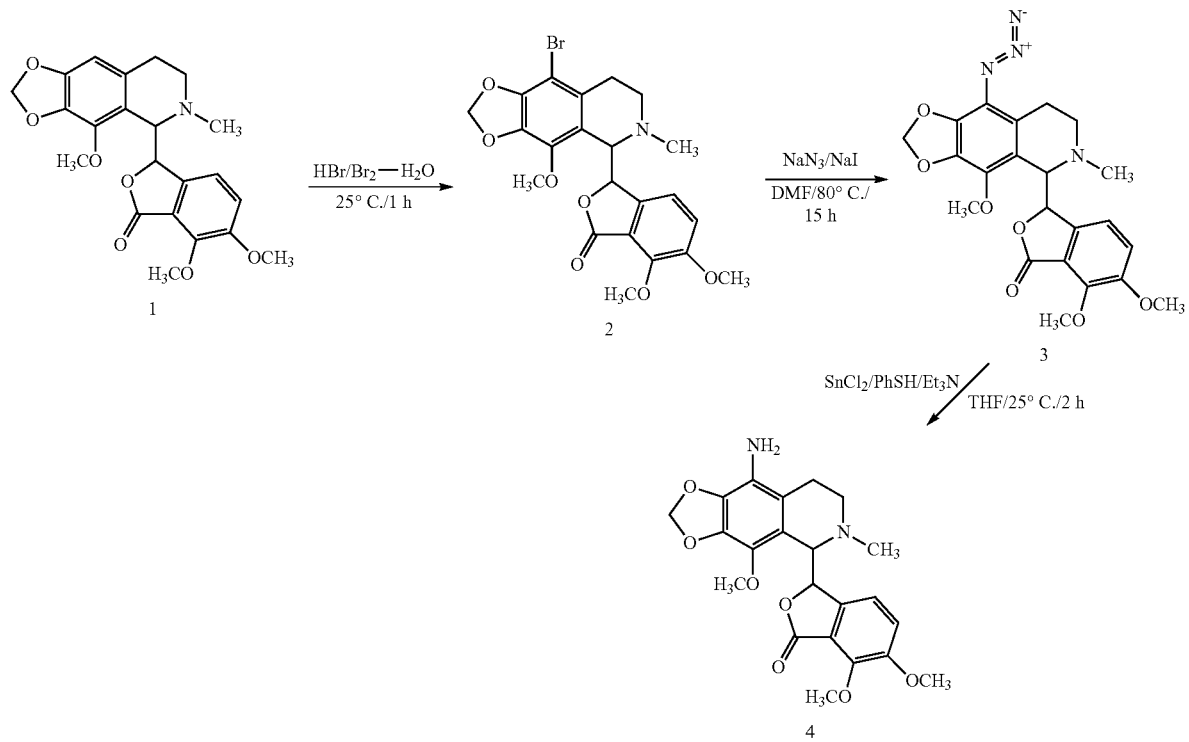

(S)-3-((R)-9-bromo-4-methoxy-6-methyl-5,6,7,8-tetrahydro-[1,3]dioxolo[4,5-g]isoquinolin-5-yl)-6,7-dimethoxyisobenzofuran-1(3H)-one (2)

To a flask containing noscapine (20 g, 48.4 mmol) was added minimum amount of 48% hydrobromic acid solution (~40 ml) to dissolve or make a suspension of the reactant. To the reaction mixture was added freshly prepared bromine water (~250 ml) drop wise until an orange precipitate appeared. The reaction mixture was then stirred at room temperature for 1 h to attain completion, neutralized to pH 10 using ammonia solution to afford solid precipitate. The solid precipitate was recrystallized with ethanol to afford bromo-substituted noscapine. Yield: 82%; mp 169-170° C.; IR: 2945 (m), 2800 (m), 1759 (s), 1612 (m), 1500 (s), 1443 (s), 1263 (s), 1091 (s), 933 (w) cm$^{-1}$; $^1$H NMR (CDCl$_3$, 400 MHz), δ 7.04 (d, 1H, J=7 Hz), 6.32 (d, 1H, J=7 Hz), 6.03 (s, 2H), 5.51 (d, 1H, J=4 Hz), 4.55 (d, 1H, J=4 Hz), 4.10 (s, 3H), 3.98 (s, 3H), 3.89 (s, 3H), 2.52 (s, 3H), 2.8-1.93 (m, 4H); $^{13}$C NMR (CDCl$_3$, 100 MHz), δ 167.5, 151.2, 150.5, 150.1, 148.3, 140.0, 135.8, 130.8, 120.3, 120.4, 120.1, 105.3, 100.9, 100.1, 87.8, 64.4, 56.1, 56.0, 55.8, 51.7, 41.2, 27.8; MS (FAB): m/z (relative abundance, %), 494 (93.8), 492 (100), 300 (30.5), 298 (35.4); MALDI: m/z 491.37 (M+), 493.34; ESI/tandem mass spectrometry: parent ion masses, 494, 492; daughter ion masses (intensity, %), 433 (51), 431 (37), 300 (100), 298 (93.3); HRMS (ESI): m/z Calcd. for $C_{22}H_{23}BrNO_7$ (M+1), 493.3211; Found, 493.3215 (M+1).

(S)-3-((R)-9-azido-4-methoxy-6-methyl-5,6,7,8-tetrahydro-[1,3]dioxolo[4,5-g]isoquinolin-5-yl)-6,7-dimethoxyisobenzofuran-1(3H)-one (3)

To a solution of compound 2 (2.0 g, 4.063 mmol) in DMF (20 mL) were added sodium azide (2.641 g, 40.63 mmol) and sodium iodide (0.609 g, 4.063 mmol) and the reaction mixture was stirred at 80° C. for 15 h to attain completion. Then the solvent was removed in vacuo and the resultant residue was dissolved in chlorofrom (40 mL), washed with water (2×40 mL), dried over sodium sulfate and concentrated to obtain the titled compound 3, which was recrystallized with ethanol in hexane (10:90) to afford brown crystals. Yield, 89%; mp 177.2-178.1° C.; IR: 1529, 1362 cm$^{-1}$; $^1$H NMR (CDCl$_3$, 400 MHz): δ 7.05 (d, 1H, J=7.0 Hz), 6.4 (d, 1H, J=7.0 Hz), 6.01 (s, 2H), 5.85 (d, 1H, J=4.4 Hz), 4.40 (d, 1H, J=4.4 Hz), 4.15 (s, 3H), 3.88 (s, 3H), 3.84 (s, 3H), 2.75-2.62 (m, 2H), 2.60-2.56 (m, 2H), 2.51 (s, 3H); $^{13}$C NMR (CDCl$_3$, 100 MHz): δ 169.2, 157.7, 152.6, 147.9, 142.2, 140.5, 135.0, 134.0, 123.5, 121.8, 119.7, 119.3, 114.1, 100.5, 87.4, 64.1, 56.7, 56.5, 56.2, 51.4, 39.2, 27.2; HRMS (ESI): m/z Calcd. for $C_{22}H_{23}N_4O_7$ (M+1), 455.4335; Found, 455.4452 (M+1).

(S)-3-((R)-9-amino-4-methoxy-6-methyl-5,6,7,8-tetrahydro-[1,3]dioxolo[4,5-g]isoquinolin-5-yl)-6,7-dimethoxyisobenzofuran-1(3H)-one (4)

To a 50-mL of round-bottomed flask containing a solution of SnCl$_2$ in THF (10 mL) were added thiophenol and triphenylamine. The reaction mixture was added slowly to a solution of azido-noscapine (3, 0.2 g, 0.440 mmol) in THF (5 mL) and the reaction mixture stirred at room temperature. The reaction progress was monitored by thin-layer chromatography at 30 minutes intervals. The reaction was found to be completed after 2 h, the solvent was removed in vacuo. The residue was diluted with chloroform (20 ml) and was added sodium hydroxide solution (20 mL). the aqueous phase was separated and extracted with chloroform (2×20 mL). the combined organic phase was dried over sodium sulfate and concentrated to obtain amino-noscapine as colorless oil, which was then treated with ethereal HCl to obtain its salt as white crystals. Yield, 83%; mp (HCl. Salt) 112.2-112.6° C.; IR: 1725, 1362 cm$^{-1}$; $^1$H NMR (CDCl$_3$, 400 MHz): δ 7.12 (d, 1H, J=7.4.0 Hz), 7.02 (d, 1H, J=7.4 Hz), 6.02 (s, 2H), 5.92 (d, 1H, J=4.0 Hz), 4.42 (d, 1H, J=4.0 Hz), 4.20 (bs, 2H), 4.02 (s, 3H), 3.85 (s, 3H), 3.80 (s, 3H), 2.74-2.64 (m, 2H), 2.61-2.56 (m, 2H), 2.52 (s, 3H); $^1$H NMR (CDCl$_3$+D$_2$O, 400 MHz): δ 7.12 (d, 1H, J=7.4.0 Hz), 7.02 (d, 1H, J=7.4 Hz), 6.02 (s, 2H), 5.92 (d, 1H, J=4.0 Hz), 4.42 (d, 1H, J=4.0 Hz), 5.12 (bs, confirms NH$_2$ group), 4.02 (s, 3H), 3.85 (s, 3H), 3.80 (s, 3H), 2.74-2.64 (m, 2H), 2.61-2.56 (m, 2H), 2.52 (s, 3H); $^{13}$C NMR (CDCl$_3$, 100 MHz): δ 169.5, 156.8, 152.6, 147.8, 142.7, 141.8, 135.0, 134.2, 123.2, 120.8, 119.9, 119.4, 114.1, 100.8, 87.6, 63.7, 56.8, 56.4, 56.1, 51.4, 39.2, 27.5; HRMS (ESI): m/z Calcd. for $C_{22}H_{24}N_2O_7$ (M+1), 428.3481; Found, 428.1562 (M+1).

HPLC Purity and Peak Attributions:

The HPLC purity was determined following two different methods using varied solvent systems.

Method 1:

Ultimate Plus, LC Packings, Dionex, C$_{18}$ column (pep Map 100, 3 μm, 100 Å particle size, ID: 1000 μm, length: 15 cm) with solvent systems A (0.1% formic acid in water) and B (acetonitrile), gradient, 25 min run at a flow of 40 μL/min. Retention time for 9-amino-nos is 18.30 min. HPLC purity was 95%.

Method 2:

Ultimate Plus, LC Packings, Dionex, C$_{18}$ column (pep Map 100, 3 μm, 100 Å particle size, ID: 1000 μm, length: 15 cm) with solvent systems A (0.1% formic acid in water) and B (methanol), gradient, 25 min run at a flow of 40 μL/min. Retention time for 9-amino-nos is 18.96 min. HPLC purity was 94%.

Other possible synthetic methods involve nitrating the aromatic ring, and reducing the nitrate group to an amine group. Such nitration and reduction reactions are well known to those of skill in the art. Ideally, methods do not involve reagents which reduce or hydrolyze the lactone moiety. In some embodiments, the lactone can be protected with a suitable protecting group, the nitro group reduced to an amine, and the lactone deprotected.

In other embodiments, the nitro group can be converted to a diazonium salt, followed by displacement to form the amine.

Other amines than 9-NH$_2$ can be formed, for example, by first forming the 9-noscapine, and then converting the 9-NH$_2$ group to another moiety using alkylation reagents in alkylation reactions. Suitable alkylation reagents as are known in the art, and include C$_{1-8}$ alkyl halides, such as alkyl bromides and iodides.

Conclusions:

Relatively simple and straightforward methods for the direct, and regioselective nitration of noscapine, which provide the nitrated product in high quantitative yields, are provided herein. A plethora of reagents and reaction conditions have been reported for reduction of aromatic nitro groups to form aromatic amine groups, though appropriate conditions need to be selected for the noscapine framework, as it is readily hydrolysable. These synthetic strategies effect the desired transformations under mild conditions.

III. Pharmaceutical Compositions

The compound, 9-aminonoscapine, and its prodrugs and metabolites, and pharmaceutically acceptable salts, as described herein, can be incorporated into pharmaceutical compositions and used to treat or prevent a condition or disorder in a subject susceptible to such a condition or disorder, and/or to treat a subject suffering from the condition or disorder. Optically active compounds can be employed as racemic mixtures, as pure enantiomers, or as compounds of varying enantiomeric purity. The pharmaceutical compositions described herein include 9-aminonoscapine, and its prodrugs and metabolites, and pharmaceutically acceptable salts, as described herein, and a pharmaceutically acceptable carrier and/or excipient.

The manner in which the compounds are administered can vary. The compositions are preferably administered orally (e.g., in liquid form within a solvent such as an aqueous or non-aqueous liquid, or within a solid carrier). Preferred compositions for oral administration include pills, tablets, capsules, caplets, syrups, and solutions, including hard gelatin capsules and time-release capsules. Compositions may be formulated in unit dose form, or in multiple or subunit doses. Preferred compositions are in liquid or semisolid form. Compositions including a liquid pharmaceutically inert carrier such as water or other pharmaceutically compatible liquids or semisolids may be used. The use of such liquids and semisolids is well known to those of skill in the art.

The compositions can also be administered via injection, i.e., intraveneously, intramuscularly, subcutaneously, intraperitoneally, intraarterially, intrathecally; and intracerebroventricularly. Intravenous administration is a preferred method of injection. Suitable carriers for injection are well known to those of skill in the art, and include 5% dextrose solutions, saline, and phosphate buffered saline. The compounds can also be administered as an infusion or injection (e.g., as a suspension or as an emulsion in a pharmaceutically acceptable liquid or mixture of liquids).

The formulations may also be administered using other means, for example, rectal administration. Formulations useful for rectal administration, such as suppositories, are well known to those of skill in the art. The compounds can also be administered by inhalation (e.g., in the form of an aerosol either nasally or using delivery articles of the type set forth in U.S. Pat. No. 4,922,901 to Brooks et al., the disclosure of which is incorporated herein in its entirety); topically (e.g., in lotion form); or transdermally (e.g., using a transdermal patch, using technology that is commercially available from Novartis and Alza Corporation). Although it is possible to administer the compounds in the form of a bulk active chemical, it is preferred to present each compound in the form of a pharmaceutical composition or formulation for efficient and effective administration.

Exemplary methods for administering such compounds will be apparent to the skilled artisan. The usefulness of these formulations may depend on the particular composition used and the particular subject receiving the treatment. These formulations may contain a liquid carrier that may be oily, aqueous, emulsified or contain certain solvents suitable to the mode of administration.

The compositions can be administered intermittently or at a gradual, continuous, constant or controlled rate to a warm-blooded animal (e.g., a mammal such as a mouse, rat, cat, rabbit, dog, pig, cow, or monkey), but advantageously are administered to a human being. In addition, the time of day and the number of times per day that the pharmaceutical formulation is administered can vary.

Preferably, the compositions are administered such that active ingredients interact with regions where cancer cells are located. The compounds described herein are very potent at treating these cancers.

In certain circumstances, the compounds described herein can be employed as part of a pharmaceutical composition with other compounds intended to prevent or treat a particular cancer, i.e., combination therapy. In addition to effective amounts of the compounds described herein, the pharmaceutical compositions can also include various other components as additives or adjuncts.

Combination Therapy

The combination therapy may be administered as (a) a single pharmaceutical composition which comprises 9-aminonoscapine as described herein, or its prodrugs or metabolites, or pharmaceutically acceptable salts, at least one additional pharmaceutical agent described herein, and a pharmaceutically acceptable excipient, diluent, or carrier; or (b) two separate pharmaceutical compositions comprising (i) a first composition comprising 9-aminonoscapine as described herein and a pharmaceutically acceptable excipient, diluent, or carrier, and (ii) a second composition comprising at least one additional pharmaceutical agent described herein and a pharmaceutically acceptable excipient, diluent, or carrier. The pharmaceutical compositions can be administered simultaneously or sequentially and in any order.

In use in treating or preventing cancer, 9-aminonoscapine can be administered together with at least one other chemotherapeutic agent as part of a unitary pharmaceutical composition. Alternatively, it can be administered apart from the other anticancer chemotherapeutic agent. In this embodiment, 9-aminonoscapine and the at least one other anticancer chemotherapeutic agent are administered substantially simultaneously, i.e. the compounds are administered at the same time or one after the other, so long as the compounds reach therapeutic levels for a period of time in the blood.

Combination therapy involves administering 9-aminonoscapine, as described herein, or a pharmaceutically acceptable salt or prodrug of 9-aminonoscapine, in combination with at least one anti-cancer chemotherapeutic agent, ideally one which functions by a different mechanism (i.e., VEGF inhibitors, alkylating agents, and the like).

Examples of known anticancer agents which can be used for combination therapy include, but are not limited to alkylating agents, such as busulfan, cis-platin, mitomycin C, and carboplatin; antimitotic agents, such as colchicine, vinblastine, paclitaxel, and docetaxel; topo I inhibitors, such as camptothecin and topotecan; topo II inhibitors, such as doxorubicin and etoposide; RNA/DNA antimetabolites, such as 5-azacytidine, 5-fluorouracil and methotrexate; DNA antimetabolites, such as 5-fluoro-2'-deoxy-uridine, ara-C, hydroxyurea and thioguanine; and antibodies, such as Herceptin® and Rituxan®. Other known anti-cancer agents, which can be used for combination therapy, include arsenic trioxide, gamcitabine, melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen and alanosine. Other classes of anti-cancer compounds that can be used in combination with 9-aminonoscapine are described below.

9-aminonoscapine can be combined with alpha-1-adrenoceptor antagonists, such as doxazosin, terazosin, and tamsulosin, which can inhibit the growth of prostate cancer cell via induction of apoptosis (Kyprianou, N., et al., Cancer Res 60:4550 4555, (2000)).

Sigma-2 receptors are expressed in high densities in a variety of tumor cell types (Vilner, B. J., et al., Cancer Res. 55: 408 413 (1995)) and sigma-2 receptor agonists, such as CB-64D, CB-184 and haloperidol, activate a novel apoptotic pathway and potentiate antineoplastic drugs in breast tumor cell lines. (Kyprianou, N., et al., Cancer Res. 62:313 322 (2002)). Accordingly, 9-aminonoscapine can be combined with at least one known sigma-2 receptor agonists, or a pharmaceutically acceptable salt of said agent.

9-aminonoscapine can be combined with lovastatin, a HMG-CoA reductase inhibitor, and butyrate, an inducer of apoptosis in the Lewis lung carcinoma model in mice, can potentiate antitumor effects (Giermasz, A., et al., Int. J. Cancer 97:746 750 (2002)). Examples of known HMG-CoA reductase inhibitors, which can be used for combination therapy include, but are not limited to, lovastatin, simvastatin, pravastatin, fluvastatin, atorvastatin and cerivastatin, and pharmaceutically acceptable salts thereof.

Certain HIV protease inhibitors, such as indinavir or saquinavir, have potent anti-angiogenic activities and promote regression of Kaposi sarcoma (Sgadari, C., et al., Nat. Med. 8:225 232 (2002)). Accordingly, 9-aminonoscapine can be combined with HIV protease inhibitors, or a pharmaceutically acceptable salt of said agent. Representative HIV protease inhibitors include, but are not limited to, amprenavir, abacavir, CGP-73547, CGP-61755, DMP-450, indinavir, nelfinavir, tipranavir, ritonavir, saquinavir, ABT-378, AG 1776, and BMS-232,632.

Synthetic retinoids, such as fenretinide (N-(4-hydroxyphenyl)retinamide, 4HPR), can have good activity in combination with other chemotherapeutic agents, such as cisplatin, etoposide or paclitaxel in small-cell lung cancer cell lines (Kalemkerian, G. P., et al., Cancer Chemother. Pharmacol. 43:145 150 (1999)). 4HPR also was reported to have good activity in combination with gamma-radiation on bladder cancer cell lines (Zou, C., et al., Int. J. Oncol. 13:1037 1041 (1998)). Representative retinoids and synthetic retinoids include, but are not limited to, bexarotene, tretinoin, 13-cis-retinoic acid, 9-cis-retinoic acid, .alpha.-difluoromethylornithine, ILX23-7553, fenretinide, and N-4-carboxyphenyl retinamide.

Proteasome inhibitors, such as lactacystin, exert anti-tumor activity in vivo and in tumor cells in vitro, including those resistant to conventional chemotherapeutic agents. By inhibiting NF-kappaB transcriptional activity, proteasome inhibitors may also prevent angiogenesis and metastasis in vivo and further increase the sensitivity of cancer cells to apoptosis (Almond, J. B., et al., Leukemia 16:433 443 (2002)). Representative proteasome inhibitors include, but are not limited to, lactacystin, MG-132, and PS-341.

Tyrosine kinase inhibitors, such as STI571 (Imatinib mesilate, Gleevec®), have potent synergetic effects in combination with other anti-leukemic agents, such as etoposide (Liu, W. M., et al. Br. J. Cancer 86:1472 1478 (2002)). Representative tyrosine kinase inhibitors include, but are not limited to, Gleevec®, ZD1839 (Iressa®), SH268, genistein, CEP2563, SU6668, SU11248, and EMD121974.

Prenyl-protein transferase inhibitors, such as farnesyl protein transferase inhibitor R115777, possess antitumor activity against human breast cancer (Kelland, L. R., et. al., Clin. Cancer Res. 7:3544 3550 (2001)). Synergy of the protein farnesyltransferase inhibitor SCH66336 and cisplatin in human cancer cell lines also has been reported (Adjei, A. A., et al., Clin. Cancer. Res. 7:1438 1445 (2001)). Prenyl-protein transferase inhibitors, including farnesyl protein transferase inhibitor, inhibitors of geranylgeranyl-protein transferase type I (GGPTase-I) and geranylgeranyl-protein transferase type-II, or a pharmaceutically acceptable salt of said agent, can be used in combination with 9-aminonoscapine. Examples of known prenylprotein transferase inhibitors include, but are not limited to, R115777, SCH66336, L-778, 123, BAL9611 and TAN-1813.

Cyclin-dependent kinase (CDK) inhibitors, such as flavopiridol, have potent, often synergetic, effects in combination with other anticancer agents, such as CPT-11, a DNA topoisomerase I inhibitor in human colon cancer cells (Motwani, M., et al., Clin. Cancer Res. 7:4209 4219, (2001)). Representative cyclin-dependent kinase inhibitors include, but are not limited to, flavopiridol, UCN-01, roscovitine and olomoucine.

Certain COX-2 inhibitors are known to block angiogenesis, suppress solid tumor metastases, and slow the growth of implanted gastrointestinal cancer cells (Blanke, C. D., Oncology (Huntingt) 16(No. 4 Suppl. 3):17 21 (2002)). Representative COX-2 inhibitors include, but are not limited to, celecoxib, valecoxib, and rofecoxib.

Any of the above-mentioned compounds can be used in combination therapy with the noscapine analogues. Further, 9-aminonoscapine can be targeted to a tumor site by conjugation with therapeutically useful antibodies, such as Herceptin® or Rituxan®, growth factors, such as DGF, NGF; cytokines, such as IL-2, IL-4, or any molecule that binds to the cell surface. The antibodies and other molecules will deliver a compound described herein to its targets and make it an effective anticancer agent. The bioconjugates can also enhance the anticancer effect of therapeutically useful antibodies, such as Herceptin® or Rituxan®.

The compounds can also be used in conjunction with surgical tumor removal, by administering the compounds before and/or after surgery, and in conjunction with radiation therapy, by administering the compounds before, during, and/or after radiation therapy.

The appropriate dose of the compound is that amount effective to prevent occurrence of the symptoms of the disorder or to treat some symptoms of the disorder from which the patient suffers. By "effective amount", "therapeutic amount" or "effective dose" is meant that amount sufficient to elicit the desired pharmacological or therapeutic effects, thus resulting in effective prevention or treatment of the disorder.

When treating cancers, an effective amount of the noscapine analogue is an amount sufficient to suppress the growth of the tumor(s), and, ideally, is a sufficient amount to shrink the tumor, and, more ideally, to destroy the tumor. Cancer can be prevented, either initially, or from re-occurring, by administering the compounds described herein in a prophylactic manner. Preferably, the effective amount is sufficient to obtain the desired result, but insufficient to cause appreciable side effects.

The effective dose can vary, depending upon factors such as the condition of the patient, the severity of the cancer, and the manner in which the pharmaceutical composition is administered. The effective dose of compounds will of course differ from patient to patient, but in general includes amounts starting where desired therapeutic effects occur but below the amount where significant side effects are observed.

The compounds, when employed in effective amounts in accordance with the method described herein, are selective to certain cancer cells, but do not significantly affect normal cells.

For human patients, the effective dose of typical compounds generally requires administering the compound in an amount of at least about 1, often at least about 10, and frequently at least about 25 µg/24 hr/patient. The effective dose generally does not exceed about 500, often does not exceed about 400, and frequently does not exceed about 300 µg/24 hr/patient. In addition, administration of the effective dose is such that the concentration of the compound within the plasma of the patient normally does not exceed 500 ng/mL and frequently does not exceed 100 ng/mL.

IV. Methods of Using the Compounds and/or Pharmaceutical Compositions

The compounds can be used to treat cancers, including blood-borne cancers and solid tumors. Representative cancers include drug-resistant ovarian cancer, drug resistant T-cell lymphoma, leukemia, non-small cell lung, colon, central nervous system (CNS), melanoma, renal, ovarian, breast and prostate cancer.

The compounds can also be used as adjunct therapy in combination with existing therapies in the management of the aforementioned types of cancers. In such situations, it is preferably to administer the active ingredients to in a manner that optimizes effects upon cancer cells, including drug resistant cancer cells, while minimizing effects upon normal cell types. While this is primarily accomplished by virtue of the behavior of the compounds themselves, this can also be accomplished by targeted drug delivery and/or by adjusting the dosage such that a desired effect is obtained without meeting the threshold dosage required to achieve significant side effects.

The following examples are provided to illustrate the present invention, and should not be construed as limiting thereof. In these examples, all parts and percentages are by weight, unless otherwise noted. Reaction yields are reported in mole percentages.

EXAMPLES

The following examples are provided to illustrate the present invention and should not be construed as limiting the scope thereof.

Example 1

Tubulin Binding Assay (Measurement of Dissociation Constant (Kd) of Noscapine and 9-Aminonoscapine with Tubulin)

Noscapine and 9-aminonoscapine (0-150 μM) were incubated with 2 μM tubulin in 25 mM PIPES, pH 6.8, 3 mM MgSO$_4$, and 1 mM EGTA for 30 min at 25° C. The fluorescence intensities of tubulin in the absence and presence of different concentrations of the agents were monitored in a JASCO FP-6500 spectrofluorometer (JASCO, Tokyo, Japan) using a cuvette of 0.3-cm path length.

The excitation wavelength was 295 nm. The inner filter effects were corrected using a formula:

$$F\text{corrected}-F\text{observed}=\text{antilog}[(A\text{ex}-A\text{em})/2],$$

where Aex and Aem are the absorbance at the excitation and emission wavelengths.

The dissociation constant (Kd) was estimated using the following equation.

$$\Delta F=\Delta F\text{max}L/(Kd+L)$$

where, ΔF is change in the fluorescence intensity of the tubulin upon binding to noscapine or 9-aminonoscapine, ΔFmax is the maximum change in the fluorescence intensity of the protein when it is fully bound with noscapine or 9-aminonoscapine, and L is the concentration of the ligand.

The ΔFmax value was calculated by the GraphPad Prism 5 software. ΔF was calculated by subtracting the fluorescence intensity of tubulin in the absence of noscapine or 9-aminonoscapine from the fluorescence intensity of tubulin in the presence of different concentrations of noscapine or 9-aminonoscapine.

The data were statistically analyzed and curve fitted using GraphPad Prism 5 software.

Sedimentation Assay

Tubulin solution was centrifuged for 10 min at 80000 g at 4° C. Soluble tubulin was measured by Bradford method. Tubulin (10 μM) was mixed with different concentrations of 9-amino-Noscapine (0, 50, 100, 15 μM) in the assembly buffer (100 mM PIPES at pH 6.8, 3 mM MgSO$_4$, 1 mM EGTA, 1 mM GTP, and 1 M sodium glutamate). A reaction control with DMSO was also set up.

Polymerization was carried on by maintaining the temperature at 37° C. in the water bath for 30 min. After polymerization, the reaction mixture was centrifuged at 120000 g at 30° C. for 30 min. The soluble tubulin content was measured by Bradford method. Polymer mass of tubulin was found out by deducting soluble tubulin mass from the total tubulin content.

Results

9-Aminonoscapine has Higher Tubulin Binding Activity than Noscapine

Tubulin, like many other proteins, contains fluorescent amino acids like tryptophans and tyrosines and the intensity of the fluorescence emission is dependent upon the microenvironment around these amino acids in the folded protein. Agents that bind tubulin typically change the micro-environment and the fluorescent properties of the target protein. Measuring these fluorescent changes has become a standard method for determining the binding properties of tubulin ligands including the classical compound colchicine. This standard method was employed to determine the dissociation constant (Kd) between tubulin and noscapine or 9-aminonoscapine.

It was determined that noscapine and 9-aminonoscapine both reduced the intrinsic fluorescence of tubulin in a concentration-dependent manner (FIGS. 1A and B). The double reciprocal plots yielded a dissociation constant (Kd) of 152±1 μM for noscapine binding to tubulin (FIG. 1C). 9-aminonoscapine was found to bind to tubulin with a Kd of 14±1 μM (FIG. 1D) suggesting that 9-aminonoscapine has a significantly higher binding affinity for tubulin than that of noscapine.

9-Aminoscapine has Negligible Effect on Tubulin Polymerization

Tubulin was polymerized in presence or absence of 9-aminonoscapine to observe its effect on polymer formation. Polymer mass of tubulin was measured by sedimentation assay. Before polymerization soluble tubulin comprises total tubulin. Total tubulin content was measured by measuring soluble tubulin by Bradford method. After polymerization, soluble tubulin content was measured and deducted from total tubulin content to find out the polymeric tubulin level.

TABLE 1

| Concentration of 9-aminonoscapine | Average % increase in polymer level |
|---|---|
| 25 μM | 2.8 ± 0.98 |
| 50 μM | 3.2 ± 3.6 |
| 100 μM | 6.3 ± 3.8 |

Table 1 indicates that 9-aminonoscapine had negligible effect on the assembly of tubulin into microtubules in vitro. 100 μM 9-amino-noscapine caused only 6.3±3.8% increase in polymeric tubulin level, indicating that it induced aggregation of tubulin at very high concentrations Having hereby disclosed the subject matter of the present invention, it should be apparent that many modifications, substitutions, and variations of the present invention are possible in light thereof. It is to be understood that the present invention can be practiced other than as specifically described. Such modifications, substitutions and variations are intended to be within the scope of the present application.

NCI 60-tumor cell line data: 9-aminonocapine is an effective anti-cancer agent that blocks cellular proliferation of a wide variety of cancer cells.

9-aminonoscapine is a potent anticancer agents that inhibits the proliferation of various human cancer cells. The panel of 60 human tumor cell lines is organized into subpanels representing leukemia, non-small cell lung, colon, CNS, melanoma, renal, ovarian, breast and prostrate cancer lines. Cells were treated with 9-aminonoscapine at increasing gradient concentrations for 48 h. The $IC_{50}$ values, which stand for the drug concentration needed to prevent cell proliferation by 50% was then measured using an in vitro Sulforhodamine B assay. Panels show bar-graphically the comparison of $IC_{50}$ values of 9-aminonoscapine (black bars) for cancer cell lines of various tissue origins.

Having hereby disclosed the subject matter of the present invention, it should be apparent that many modifications, substitutions, and variations of the present invention are possible in light thereof. It is to be understood that the present invention can be practiced other than as specifically described. Such modifications, substitutions and variations are intended to be within the scope of the present application.

The invention claimed is:

1. A method of treating cancer in a patient, comprising administering an effective amount of a compound having one of the following formulas:

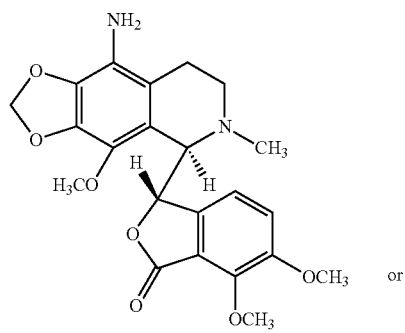 or

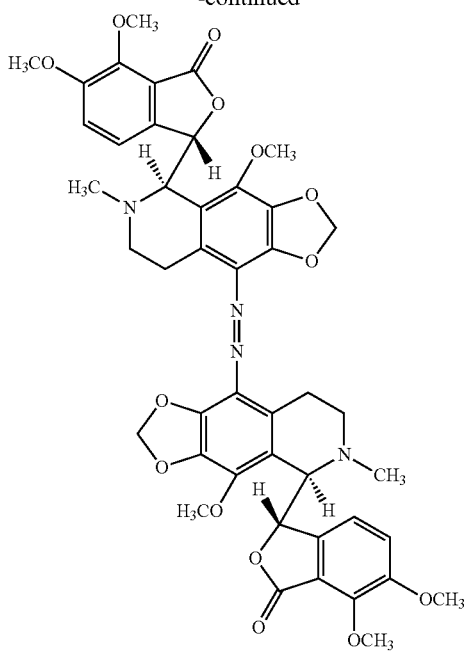

and pharmaceutically acceptable salts thereof to a patient in need of treatment thereof.

2. The method of claim 1, wherein the cancer is selected from the group consisting of drug-resistant ovarian cancer, drug resistant T-cell lymphoma, leukemia, non-small cell lung, colon, central nervous system (CNS), melanoma, renal, ovarian, breast and prostate cancer.

3. The method of claim 2, wherein the cancer is drug-resistant ovarian cancer or T-cell lymphoma.

4. The method of claim 1, wherein the cancer is a drug-resistant cancer.

* * * * *